US012638320B2

(12) United States Patent
Akhbari et al.

(10) Patent No.: US 12,638,320 B2
(45) Date of Patent: May 26, 2026

(54) ULTRASOUND TIME-OF-FLIGHT SENSOR MODULE, ULTRASOUND ABSORPTION SENSOR MODULE, TACTILE-SENSING SYSTEMS, AND RELATED METHODS

(71) Applicant: UltraSense Systems, Inc., San Jose, CA (US)

(72) Inventors: Sina Akhbari, San Jose, CA (US); Hao-Yen Tang, San Jose, CA (US)

(73) Assignee: UltraSense Systems, Inc., San Jose, CA (US)

( * ) Notice: Subject to any disclaimer, the term of this patent is extended or adjusted under 35 U.S.C. 154(b) by 889 days.

(21) Appl. No.: 17/970,117

(22) Filed: Oct. 20, 2022

(65) Prior Publication Data

US 2023/0122547 A1 Apr. 20, 2023

Related U.S. Application Data

(60) Provisional application No. 63/257,684, filed on Oct. 20, 2021.

(51) Int. Cl.
*G01F 1/667* (2022.01)
*A61B 8/00* (2006.01)
(Continued)

(52) U.S. Cl.
CPC .............. *G01F 1/667* (2013.01); *A61B 8/00* (2013.01); *B25J 13/084* (2013.01); *G01S 15/8915* (2013.01)

(58) Field of Classification Search
CPC ...... B25J 13/084; B25J 13/085; B25J 19/026; B25J 19/028; G01S 15/8915; G01S 15/88; G01L 1/162; G01L 5/226
See application file for complete search history.

(56) References Cited

U.S. PATENT DOCUMENTS 4,412,544 A 11/1983 Beretsky et al.
8,359,931 B2 * 1/2013 Nishiwaki ............... B66C 1/445
73/846

(Continued)

FOREIGN PATENT DOCUMENTS

GB 2606534 A * 11/2022 ............. G01N 29/28
WO WO2018077761 5/2018
WO WO-2022238368 A1 * 11/2022 ........... G01N 29/265

*Primary Examiner* — Pedro J Cuevas
(74) *Attorney, Agent, or Firm* — Perkins Coie LLP

(57) ABSTRACT

An ultrasound time-of-flight (TOF) sensor module includes an ultrasonic transducer device, a cover layer, an elastic member, and a signal processor electronically coupled to the ultrasonic transducer. The ultrasonic transducer device includes at least one ultrasonic transducer, which is configured as an ultrasonic transmitter and/or an ultrasonic receiver. The elastic member is interposed between the ultrasonic transducer device and the cover layer. The elastic member undergoes reversible compression in response to an external object impacting and/or contacting the cover layer. An ultrasound propagation distance between the ultrasonic transducer and the cover layer varies in accordance with the compression. The ultrasonic transmitter(s) transmit ultrasound signals. The cover layer reflects a fraction f of the ultrasound signals incident thereon. The signal processor obtains TOF data which indicate time differences between times of transmission of transmitted ultrasound signals by the ultrasonic transmitter(s) and times of receipt of reflected ultrasound signals by the ultrasonic receiver(s). The time differences vary in accordance with the ultrasound propagation distance.

23 Claims, 13 Drawing Sheets

(51) Int. Cl.
B25J 13/08 (2006.01)
G01S 15/89 (2006.01)

(56) References Cited

U.S. PATENT DOCUMENTS

| | | | | |
|---|---|---|---|---|
| 8,421,642 B1* | 4/2013 | McIntosh | H04L 67/12 | |
| | | | 482/8 | |
| 8,573,069 B2* | 11/2013 | Nishiwaki | B25J 13/083 | |
| | | | 73/862.471 | |
| 8,640,551 B2* | 2/2014 | Nishiwaki | B66C 13/16 | |
| | | | 73/846 | |
| 8,676,540 B1 | 3/2014 | Welch et al. | | |
| 9,127,999 B2* | 9/2015 | Tsuruno | G01L 1/25 | |
| 9,265,462 B2* | 2/2016 | McIntosh | H04L 67/12 | |
| 9,642,571 B2* | 5/2017 | McIntosh | G06F 3/04883 | |
| 10,466,844 B1 | 11/2019 | Tang et al. | | |
| 10,585,534 B2 | 3/2020 | Tang et al. | | |
| 10,719,175 B2 | 7/2020 | Akhbari et al. | | |
| 10,775,938 B2 | 9/2020 | Tang et al. | | |
| 11,426,764 B2* | 8/2022 | Wiest | G01S 7/521 | |
| 11,775,073 B1* | 10/2023 | Tang | G06F 3/167 | |
| | | | 345/174 | |
| 12,050,732 B2* | 7/2024 | Tang | G06F 3/167 | |
| 12,109,684 B2* | 10/2024 | Nagakari | G01L 5/228 | |
| 2001/0000666 A1 | 5/2001 | Wood et al. | | |
| 2002/0005108 A1 | 1/2002 | Ludwig | | |
| 2003/0144814 A1 | 7/2003 | Hama et al. | | |
| 2003/0217873 A1 | 11/2003 | Paradiso et al. | | |
| 2003/0233233 A1 | 12/2003 | Hong | | |
| 2007/0260425 A1 | 11/2007 | Kim | | |
| 2008/0316184 A1 | 12/2008 | D'Souza | | |
| 2009/0157206 A1 | 6/2009 | Weinberg et al. | | |
| 2009/0224161 A1 | 9/2009 | Fritsch et al. | | |
| 2010/0117993 A1 | 5/2010 | Kent | | |
| 2010/0139991 A1 | 6/2010 | Phillip et al. | | |
| 2010/0258361 A1 | 10/2010 | Yamauchi et al. | | |
| 2010/0268503 A1* | 10/2010 | Specht | A61B 8/587 | |
| | | | 73/1.82 | |
| 2011/0061464 A1 | 3/2011 | Yi-min | | |
| 2011/0121591 A1* | 5/2011 | Nishiwaki | B66C 13/16 | |
| | | | 901/46 | |
| 2012/0174672 A1* | 7/2012 | Tsuruno | B25J 13/083 | |
| | | | 73/627 | |
| 2012/0274609 A1 | 11/2012 | Sheng et al. | | |
| 2013/0225982 A1* | 8/2013 | McIntosh | A61B 5/0024 | |
| | | | 600/587 | |
| 2013/0345864 A1 | 12/2013 | Park et al. | | |
| 2014/0022189 A1 | 1/2014 | Sheng et al. | | |
| 2014/0071095 A1 | 3/2014 | Godsill | | |
| 2015/0148674 A1 | 5/2015 | Park et al. | | |
| 2015/0169136 A1 | 6/2015 | Ganti et al. | | |
| 2016/0143577 A1* | 5/2016 | McIntosh | G06F 3/0346 | |
| | | | 600/595 | |
| 2016/0216794 A1 | 7/2016 | Yoon et al. | | |
| 2016/0246449 A1 | 8/2016 | Jarske | | |
| 2017/0110504 A1 | 4/2017 | Panchawagh et al. | | |
| 2017/0255338 A1 | 9/2017 | Medina | | |
| 2017/0322290 A1 | 11/2017 | Ng et al. | | |
| 2017/0336903 A1 | 11/2017 | Rivaud et al. | | |
| 2017/0336926 A1 | 11/2017 | Chaudhri et al. | | |
| 2018/0032161 A1 | 2/2018 | Shi et al. | | |
| 2018/0032211 A1 | 2/2018 | King | | |
| 2018/0039392 A1 | 2/2018 | Kim et al. | | |
| 2018/0164937 A1 | 6/2018 | Lynn | | |
| 2018/0246612 A1 | 8/2018 | Lynn et al. | | |
| 2018/0276439 A1 | 9/2018 | Strohmann et al. | | |
| 2018/0276440 A1 | 9/2018 | Strohmann et al. | | |
| 2018/0284892 A1 | 10/2018 | Kwon et al. | | |
| 2018/0323783 A1* | 11/2018 | Bang | G01S 15/88 | |
| 2019/0050618 A1 | 2/2019 | Khuri-Yakub | | |
| 2019/0074833 A1 | 3/2019 | Sheng | | |
| 2019/0354209 A1 | 11/2019 | Tang | | |
| 2019/0354210 A1 | 11/2019 | Akhbari et al. | | |
| 2019/0354237 A1 | 11/2019 | Tang et al. | | |
| 2019/0354238 A1 | 11/2019 | Akhbari et al. | | |
| 2021/0181041 A1 | 6/2021 | Tang | | |
| 2021/0239553 A1 | 8/2021 | Akhbari et al. | | |
| 2021/0242393 A1 | 8/2021 | Tang | | |
| 2021/0278926 A1 | 9/2021 | Akhbari et al. | | |
| 2021/0293641 A1 | 9/2021 | Tu et al. | | |
| 2021/0293648 A1 | 9/2021 | Tu et al. | | |
| 2024/0028124 A1* | 1/2024 | Tang | G06F 3/167 | |
| 2024/0210361 A1* | 6/2024 | Aretos | G01N 29/226 | |

* cited by examiner

640

Start

Configure force-measuring device ← 642

Impact and/or contact ← 644

Obtain impact data ← 646

End

ULTRASOUND TIME-OF-FLIGHT SENSOR MODULE, ULTRASOUND ABSORPTION SENSOR MODULE, TACTILE-SENSING SYSTEMS, AND RELATED METHODS

CROSS-REFERENCE TO RELATED APPLICATION(S)

This application claims the benefit of U.S. Provisional Patent Application No. 63/257,684 filed on Oct. 20, 2021, entitled "ULTRASOUND TIME-OF-FLIGHT SENSOR MODULE, ULTRASOUND ABSORPTION SENSOR MODULE, TACTILE-SENSING SYSTEMS, AND RELATED METHODS," which is incorporated herein by reference in its entirety.

BACKGROUND

Many tactile sensors have been developed based on piezoelectric, piezoresistive, capacitive, and other principles. Tactile sensors can be applied to robotic systems to enable interaction with objects in the environment in a manner similar to humans. There are opportunities for improving the functionality of tactile-sensing systems, such as determining the rigidity of and/or identifying the material of external objects. The present disclosure relates to improved tactile sensors that employ ultrasonic transducer devices. For example, such ultrasonic devices can be integrated circuits (ICs) containing piezoelectric micromechanical ultrasonic transducers (PMUTs). According to the present disclosure, the ultrasonic transducer devices can be configured to conduct ultrasound time-of-flight measurements or ultrasound absorption measurements.

SUMMARY OF THE INVENTION

In one aspect, an ultrasound time-of-flight sensor module includes an ultrasonic transducer device, a cover layer, an elastic member, and a signal processor electronically coupled to the ultrasonic transducer. The ultrasonic transducer device includes at least one ultrasonic transducer. Each ultrasonic transducer is configured as an ultrasonic transmitter and/or an ultrasonic receiver. The elastic member is interposed between the ultrasonic transducer device and the cover layer and mechanically coupled to the cover layer and to the ultrasonic transducer device. The elastic member undergoes reversible compression in response to an external object impacting and/or contacting the cover layer, an ultrasound propagation distance between the ultrasonic transducer and the cover layer varying in accordance with the compression. The ultrasonic transmitter(s) are configured to transmit ultrasound signals (transmitted ultrasound signals) towards the cover layer. The cover layer is configured to reflect a fraction f of ultrasound signals incident thereon (reflected ultrasound signals). The ultrasonic receiver(s) are configured to receive reflected ultrasound signals. The signal processor is configured to obtain time-of-flight data indicating time differences between times of transmission of transmitted ultrasound signals by the ultrasonic transmitter(s) and times of receipt of reflected ultrasound signals by the ultrasonic receiver(s). The time differences vary in accordance with the ultrasound propagation distance.

In another aspect, a tactile-sensing system includes the ultrasound time-of-flight sensor module, configured to be positioned at a tactile edge. The signal processor is configured to obtain at least one-tactile related data from the ultrasound time-of-flight data when the external object impacts and/or contacts the cover layer.

In yet another aspect, an ultrasound absorption sensor module includes an ultrasonic transducer device, a deformable member mechanically coupled to the ultrasonic transducer device and configured to conform to a contour of an external object that impacts and/or contacts an outer surface of the deformable member, and a signal processor electronically coupled to the ultrasonic transducer. The ultrasonic transducer device includes at least one ultrasonic transducer. Each ultrasonic transducer is configured as an ultrasonic transmitter and/or an ultrasonic receiver. The ultrasonic transmitter(s) are configured to transmit ultrasound signals (transmitted ultrasound signals) towards the outer surface. A first fraction $f_1$ of transmitted ultrasound signals is absorbed by the external object impacting and/or contacting the outer surface. A second fraction $f_1$ of the transmitted ultrasound signals is received by the ultrasonic receiver(s) (received ultrasound signals). The second fraction $f_2$ is $1-f_1$ or less. The signal processor is configured to obtain ultrasound absorption data in accordance with the transmitted ultrasound signals and the received ultrasound signals.

In yet another aspect, a tactile-sensing system includes the ultrasound absorption sensor module, configured to be positioned at a tactile edge. The signal processor is configured to obtain at least one-tactile related data from the ultrasound absorption data when the external object impacts and/or contacts the outer surface.

In yet another aspect, an impact-sensing system includes a force-measuring device including a piezoelectric force-measuring element and a signal processor electronically coupled to the piezoelectric force-measuring element. The force-measuring device is positioned near an impact region. The signal processor is configured to obtain impact data in accordance with mechanical deformation of the piezoelectric force-measuring element resulting from an external object impacting and/or contacting the impact region.

In yet another aspect, a tactile-sensing method includes the following steps. Step (A1) includes configuring an ultrasound time-of-flight sensor module positioned at a tactile edge. The ultrasound time-of-flight sensor module includes (1) an ultrasonic transducer device including at least one ultrasonic transducer, each ultrasonic transducer being configured as an ultrasonic transmitter and/or an ultrasonic receiver, (2) a cover layer, and (3) an elastic member interposed between the ultrasonic transducer device and the cover layer and mechanically coupled to the cover layer and to the ultrasonic transducer device. Step (A2) includes moving the tactile edge towards an external object and/or moving the external object towards the tactile edge such that the external object impacts and/or contacts the cover layer and the elastic member undergoes reversible compression. An ultrasound propagation distance between the ultrasonic transducer and the cover layer varies in accordance with the compression. Step (A3) includes transmitting, by the ultrasonic transmitter(s), ultrasound signals (transmitted ultrasound signals) towards the cover layer. Step (A4) includes reflecting, by the cover layer, a fraction f of ultrasound signals incident thereon (reflected ultrasound signals). Step (A5) includes receiving, by the ultrasonic receiver(s), the reflected ultrasound signals. Step (A6) includes obtaining, by a signal processor, time-of-flight data at least in part from the reflected ultrasound signals. representing time differences between times of transmission of transmitted ultrasound signals by the ultrasonic transmitter(s) and times of receipt of reflected ultrasound signals by the ultrasonic receiver(s). The time-of-flight data indicate time differences between times of transmission of transmitted ultrasound signals by the ultrasonic transmitter(s) and times of receipt of reflected ultrasound signals by the ultrasonic receiver(s). The time differences vary in accordance with the ultrasound propagation distance. Step (A7) includes determining, by the signal processor, at least one tactile-related data of the external object from the time-of-flight data.

In yet another aspect, a tactile-sensing method includes the following steps. Step (B1) includes configuring an ultrasound absorption sensor module positioned at a tactile edge. The ultrasound absorption sensor module includes (1) an ultrasonic transducer device including at least one ultrasonic transducer, each ultrasonic transducer being configured as an ultrasonic transmitter and/or an ultrasonic receiver, and (2) a deformable member mechanically coupled to the ultrasonic transducer device and configured to conform to a contour of an external object that impacts and/or contacts an outer surface of the deformable member. Step (B2) includes moving the tactile edge towards the external object and/or moving the external object towards the tactile edge such that the external object impacts and/or contacts the outer surface of the deformable member and the deformable member conforms to the contour of the external object. Step (B3) includes transmitting, by the ultrasonic transmitter(s), ultrasound signals (transmitted ultrasound signals) towards the outer surface. A first fraction $f_1$ of transmitted ultrasound signals is absorbed by the external object impacting and/or contacting the outer surface. Step (B4) includes receiving, by the ultrasound receiver(s), a second fraction $f_2$ of the transmitted ultrasound signals (received ultrasound signals). The second fraction $f_1$ is $1-f_1$ or less. Step (B5) includes obtaining, by a signal processor, ultrasound absorption data in accordance with the transmitted ultrasound signals and the received ultrasound signals. Step (B6) includes determining, by the signal processor, at least one tactile-related data of the external object from the ultrasound absorption data.

In yet another aspect, an impact-sensing method includes the following steps. Step (C1) includes configuring a force-measuring device positioned near an impact region. The force-measuring device includes a piezoelectric force-measuring element. Step (C2) includes moving the impact region towards an external object and/or moving the external object towards the impact region such that the external object impacts and/or contacts the impact region. Step (C3) includes obtaining, by a signal processor, impact data in accordance with mechanical deformation of the piezoelectric force-measuring element resulting from the impact and/or contact.

The above summary of the present invention is not intended to describe each disclosed embodiment or every implementation of the present invention. The description that follows more particularly exemplifies illustrative embodiments. In several places throughout the application, guidance is provided through examples, which examples can be used in various combinations. In each instance of a list, the recited list serves only as a representative group and should not be interpreted as an exclusive list.

BRIEF DESCRIPTION OF THE FIGURES

The disclosure may be more completely understood in consideration of the following detailed description of various embodiments of the disclosure in connection with the accompanying drawings, in which.

DETAILED DESCRIPTION OF ILLUSTRATIVE EMBODIMENTS

The present disclosure relates to user-input systems, user-input modules, and methods of detecting a user-input at a cover member of a user-input system.

In this disclosure:

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

The recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. As appropriate, any combination of two or more steps may be conducted simultaneously.

Figure 1:
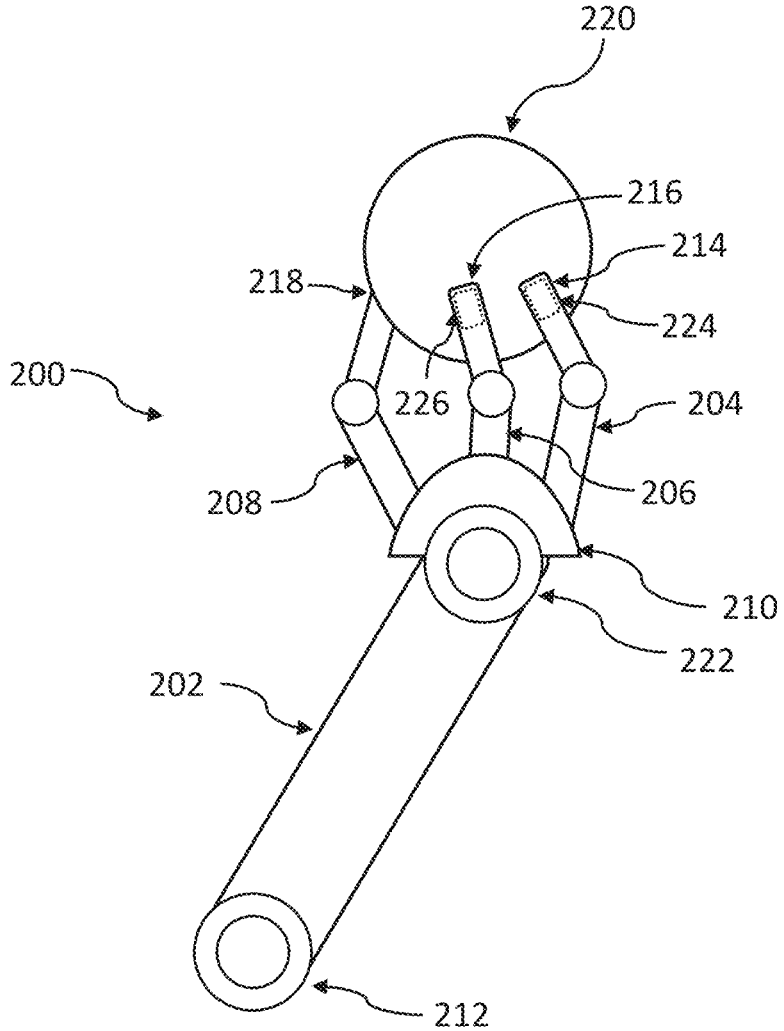
FIG. 1 is a schematic side view of an implementation of tactile-sensing systems in a robotic arm.

FIG. 1 is a schematic side view of a robotic arm 200, which includes a robotic arm segment 202, a robotic hand 210, and robotic fingers 204, 206, and 208 extending from the robotic hand 210. The robotic arm 200 may be connected to a torso portion of a robotic system at a first connector 212 of the robotic arm 202. The robotic arm segment 202 is connected to the robotic hand 210 at a second connector 222 of the robotic arm segment 202. The robotic arm 200 can be used to provide tactile information about external objects. In the example shown, an external object 220 (e.g., a ball) is being held (grasped) by the three fingers 204, 206, and 208 at their respective fingertips 214, 216, and 218. In the example shown, tactile-sensing systems 224, 226 are positioned at the fingertips 214, 216, respectively. More specifically, the tactile-sensing systems 224, 226 are positioned at tactile edges. A tactile edge is a surface or an extremity of a system (for example, a robot or robotic arm) that impacts and/or contacts an external object, where tactile-related data can be obtained. In this case, the tactile edge is a portion of the fingertip (214, 216) or finger (204, 206) that contacts the external object 220.

Figure 2:
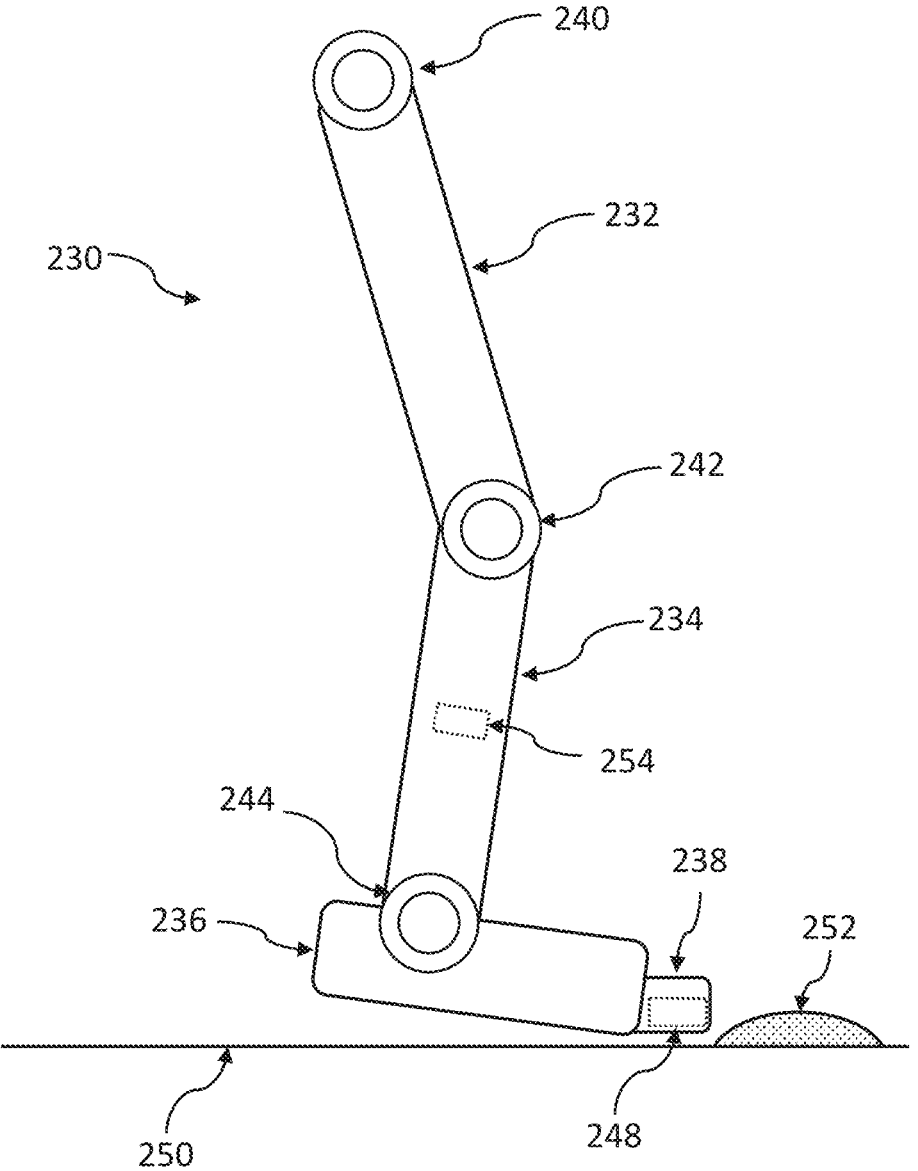
FIG. 2 is a schematic side view of implementations of a tactile-sensing system and an impact-sensing system in a robotic leg.

FIG. 2 is a schematic side view of a robotic leg 230, which includes a first robotic leg segment 232, a second robotic leg segment 234, a robotic foot 236, and a robotic toe 238. The robotic leg 230 may be connected to a torso portion of a robotic system at a first connector 240 of the first robotic leg segment 232. Typically, a robotic system is equipped with two or more robotic legs (230). The robotic system can move throughout the environment by coordinating the movement of the robotic leg segments (232, 234) and robotic feet (236) of each of the two or more robotic legs (230). The first robotic leg segment 232 and the second robotic leg segment 234 are connected to each other at a second connector 242. The second robotic leg segment 234 and the robotic foot are connected to each other at a third connector 244. The robotic toe 238 extends from the robotic foot 236. The robotic leg 230 can be used to provide tactile-related data about external objects (e.g., a bump 252 protruding from the ground 250). In the example shown, the robotic toe 238 impacts and/or contacts an external object 252. Alternatively, we can state that the external object 252 impacts and/or contacts the robotic toe 238. In the example shown, a tactile-sensing system 248 is positioned at the robotic toe 238. More specifically, the tactile-sensing system 248 is positioned at a tactile edge. In this case, the tactile edge is a portion of the toe 238 that contacts the external object 252.

The robotic leg 230 additionally includes an impact-sensing system 254. The impact-sensing system 254 obtains data relating to the impact of the robotic leg 230 (including, for example, the impact of the robotic foot 236 and/or the robotic toe 238) on the ground 250 and/or external objects 252. In the example shown, the impact-sensing system 254 is mounted to the second robotic leg segment 234. In other cases, the impact-sensing system 254 can be mounted elsewhere in the robotic leg 230, such as to the first robotic leg segment 232, to the robotic foot 236, or to the robotic toe 238. It is not necessary that the impact-sensing system 254 be positioned at the impact region (i.e., the portion of the toe 238 that impacted by the external object 252). Nevertheless, the impact-sensing system 254 should be positioned sufficiently close to the impact region, such that the impact-sensing system 254 can effectively obtain the impact data for impact events occurring at the impact region.

Figure 3:
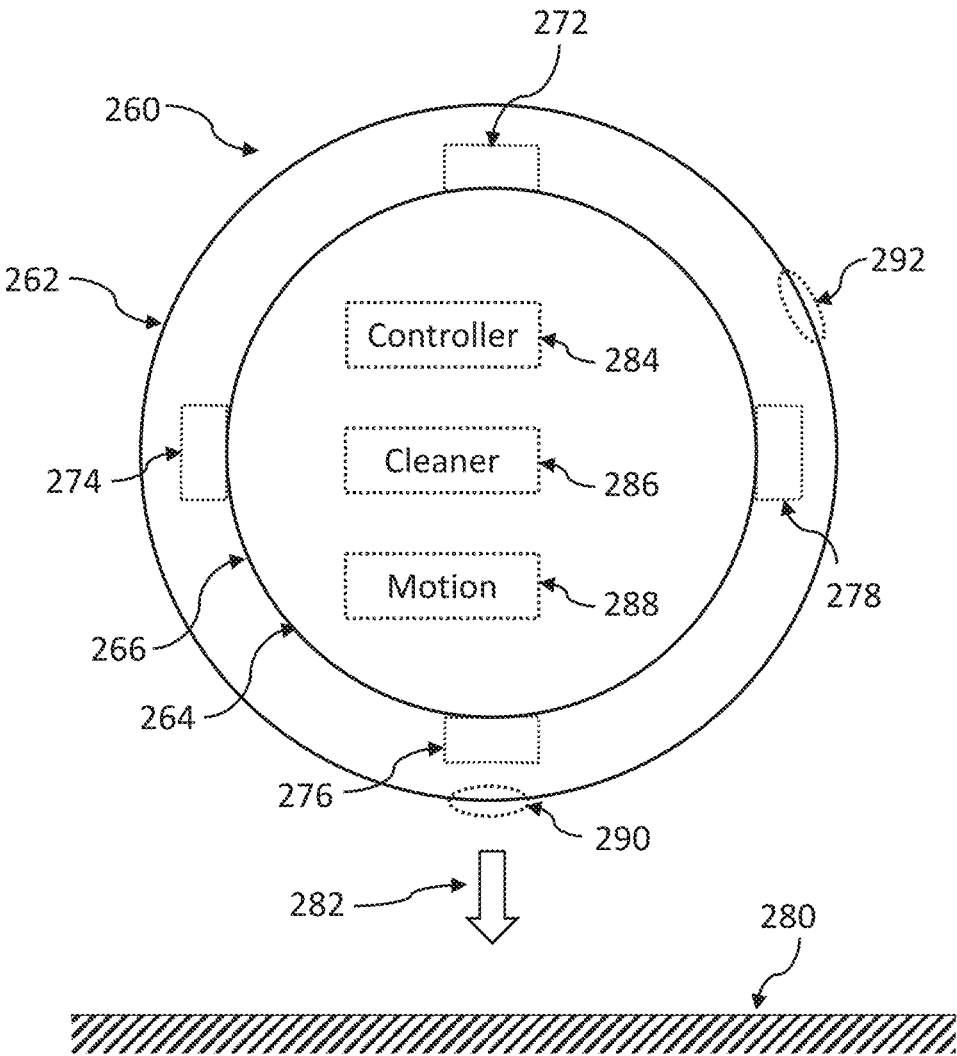
FIG. 3 is a schematic top view of implementations of impact sensing systems in a floor-cleaning robot.

FIG. 3 is a schematic top view of a floor-cleaning robot 260. The floor-cleaning robot 260 has an approximately circular shape in the top view and includes an outer housing (shroud) 262 and an internal assembly 264. In the example shown, the internal assembly 264 includes four impact-sensing systems (272, 274, 276, 278), mounted to an outer perimeter 266 of the internal assembly 264. Accordingly, the impact-sensing systems are protected from direct contact with external objects but are close to the points of impact. The internal assembly 264 additionally includes a controller system 284, a cleaning system 286, and a motion system 288. The cleaning system 286 cleans a floor of a room and the motion system 288 moves the robot 260 across the room. In the example shown, there is one impact-sensing system for each quadrant of the robot 260. In the example shown, the motion system 288 is moving the robot towards a wall 280 of the room, along a direction indicated by an arrow 282. At time of impact between the floor-cleaning robot 260 and the wall 280, the impact-sensing systems 272, 274, 276, 278 will obtain their respective impact data. For example, the impact-sensing system 276, which is closest to the impact region 290, may record a larger magnitude of impact than the other impact-sensing systems (272, 274, 278). The controller 284 receives impact data from the impact-sensing systems (272, 274, 276, 278), calculates a new desired trajectory for the floor-cleaning robot 260, and instructs the motion system 288 to move the floor-cleaning robot 260 according to the new desired trajectory.

In the example shown, the wall 280 is the external object which is impacted by the impact region 290. The impact region can change according to the trajectory of the floor-cleaning robot 260. For example, during another trajectory, the impact region might be at 292. In that case, the impact-sensing system 278, which is closest to the impact region 292, may record a larger magnitude of impact than the other impact-sensing systems (272, 274, 276).

Figure 4:
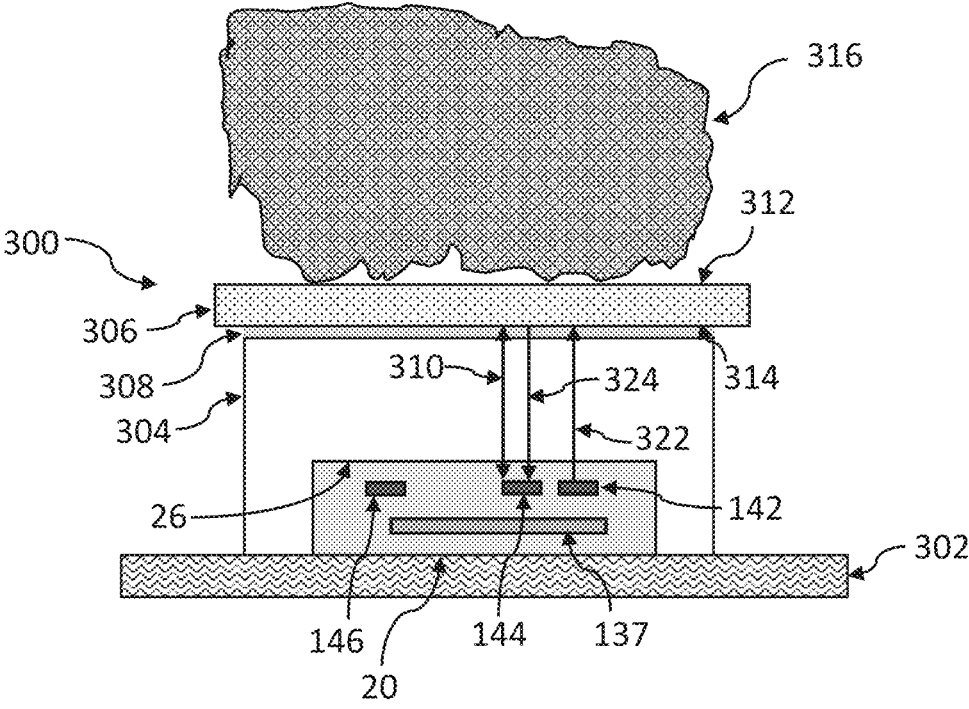
FIG. 4 is a schematic side view of an ultrasound time-of-flight sensor module which can be configured as a tactile-sensing system.

FIG. 4 is schematic side view of an ultrasound time-of-flight (TOF) sensor module 300. The ultrasound TOF sensor module can be configured as a tactile-sensing system as explained below. The ultrasound TOF sensor module 300 includes an ultrasonic transducer device 20, a cover layer 306, and an elastic member 304 interposed between the ultrasonic transducer device 20 and the cover layer 306. The ultrasonic transducer device 20 can be a packaged integrated circuit (IC). The elastic member 304 can contain rubber or plastic. For example, the elastic member 304 can be more deformable than the cover layer 306. The elastic member 304 is mechanically coupled to the cover layer 306 and to the ultrasonic transducer device 20. For example, the cover layer can be adhered to the elastic member 304 via an adhesive layer 308 between the inner surface 314 of the cover layer 306 and elastic member 304. In the example shown, the ultrasonic transducer device 20 is a packaged integrated circuit (IC), mounted to a circuit substrate 302. For example, the elastic member 304 can be molded on the circuit substrate 302 to encapsulate the ultrasonic transducer IC 20.

In the example shown, an external object 316 (e.g., a rock) is impacting and/or contacting the cover layer 306 at its outer surface 312. The cover layer 306 is configured to reflect ultrasound signals. For example, the cover layer contains a metal, such as aluminum. The elastic member 304 undergoes reversible compression in response to an external object (316) impacting and/or contacting the cover layer 306. When the external object is moved away from the cover layer 306, the elastic member 304 reverts to its uncompressed state. The ultrasonic transducer device 20 includes ultrasonic transducers 142, 144. Each ultrasonic transducer can be configured as an ultrasonic transmitter and/or an ultrasonic receiver. In the example shown, ultrasonic transducer 142 is configured as an ultrasonic transmitter and an ultrasonic transducer 144 is configured as an ultrasonic receiver. An ultrasonic transducer device includes at least one ultrasonic transducer. Furthermore, an ultrasonic transducer device includes at least one ultrasonic transmitter and at least one ultrasonic receiver.

The ultrasonic transmitter 142 is configured to transmit ultrasound signals (transmitted ultrasound signals). At least a portion of the transmitted ultrasound signals exits the ultrasonic transducer device 20 through its ultrasound transmission surface (top surface) 26 and propagates towards the cover layer 306. For simplicity, the transmitted ultrasound signals are represented as arrow 322 pointing to the cover layer 306 even though some of the transmitted ultrasound signals may not travel towards the cover layer 306. The cover layer 306 is configured to reflect a fraction f of the ultrasound signals incident thereon (reflected ultrasound signals). For example, the cover layer is chosen so that the fraction f is at least 50%. The reflected ultrasound signals are indicated by arrow 324. The ultrasonic receiver 144 is configured to receive the reflected ultrasound signals 324. The ultrasound propagation distance 310 is a separation distance between the ultrasonic transducer (142, 144) and the cover layer. The ultrasound propagation distance varies in accordance with the compression of the elastic member. An ultrasound signal that traverses one round trip, from the ultrasonic transmitter 142, to the cover layer 306, to the ultrasonic receiver 144, travels approximately twice the ultrasound propagation distance 310.

The ultrasound TOF sensor module 300 additionally includes a signal processor 137 electronically coupled to the ultrasonic transducer(s) 142, 144. In the example shown, the signal processor 137 is housed in the ultrasonic transducer device 20. Alternatively, the signal processor can be implemented as a separate IC and mounted on the circuit substrate 302. The signal processor 137 is configured to obtain time-of-flight (TOF) data. TOF data represents time differences $\tau$ between times of transmission of transmitted ultrasound signals 322 by the ultrasonic transmitter(s) 142 and times of receipt of reflected ultrasound signals 324 by the ultrasonic receiver(s) 144. Consider a simple example of a $\Delta T$ calculation. Suppose that in the uncompressed state, the separation distance 310 (ultrasound propagation distance) between the cover layer 306 and the ultrasonic transducers 142, 144 is approximately 2000 $\mu$m, and that an average speed of sound in the sound propagation medium (e.g., primarily the elastic member, as well as the adhesive layer 308 and materials of the ultrasonic transducer IC 20) is 1000 m/sec. The time difference $\Delta T$ for the ultrasound waves to make one round trip from the ultrasonic transmitter 142, to the cover layer 306, and then to the ultrasonic receiver 144, is approximately 4000 $\mu$m/(1000 m/sec)=4 $\mu$s. If the ultrasound propagation distance is decreased by 10%, the time difference $\Delta T$ will decrease by approximately 400 ns. Time differences $\Delta T$ can be obtained for the first round trip and for subsequent round trips of the ultrasound signals.

Factors such as the rigidity of the external object (e.g., a rock or soil) and the magnitude of impact (force) determine the compression of the elastic member. Since the time differences $\Delta T$ vary in accordance with the ultrasound propagation distance, and the ultrasound propagation distances vary in accordance with the compression of the elastic member, the ultrasound TOF data can help to determine the rigidity of the external object. Additionally, it may be possible to determine or infer a material characteristic of the external object from the rigidity of the object. Accordingly, an ultrasound TOF sensor module 300 can be configured as a tactile-sensing system (e.g., 214, 216, 248). A tactile-sensing system can include an ultrasound TOF sensor module 300, configured to be positioned at a tactile edge. Additionally, the signal processor 137 can be configured to obtain at least one at least one tactile-related data from the ultrasound time-of-flight data when the external object 316 impacts and/or contacts the cover layer 306. The ultrasound TOF sensor module 300 can be configured to be mounted to a robot. The signal processor is configured to obtain TOF data, such as $\Delta T$ values before and during compression of the elastic member, when the cover layer impacts the external object. The signal processor can be configured to obtain tactile-related data from the ultrasound TOF data. For example, tactile-related data can include data relating to rigidity of the external object. Furthermore, the signal processor can be configured to obtain tactile-related data including a material characteristic of the external object.

Figure 5:
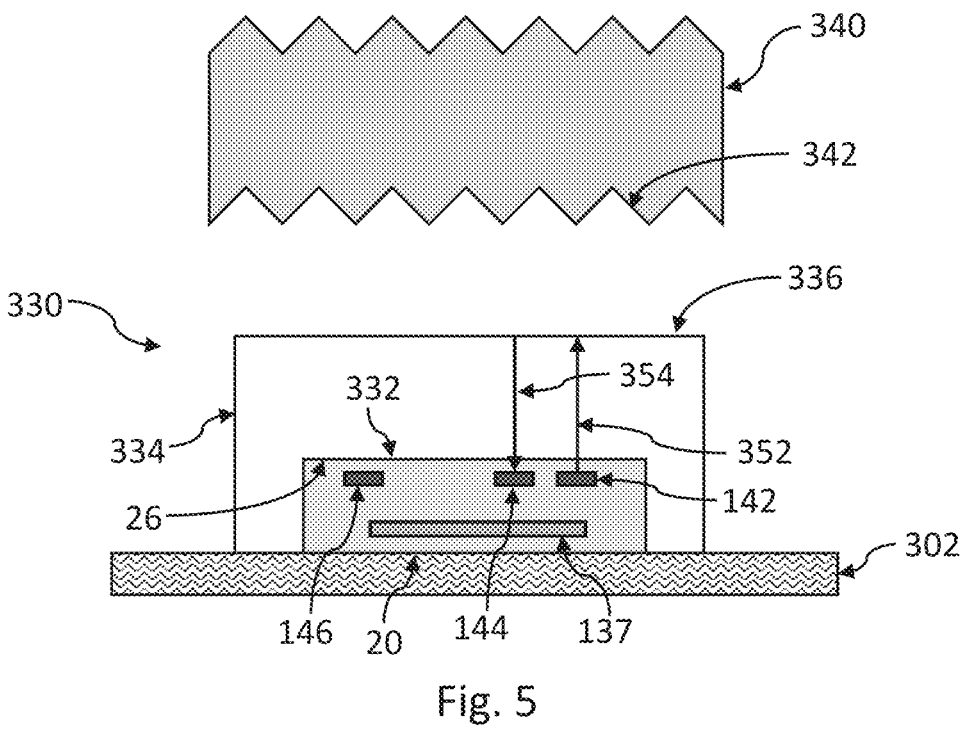
FIGS. 5 and 6 are schematic side views of an ultrasound absorption sensor module which can be configured as a tactile-sensing system.
Figure 6:
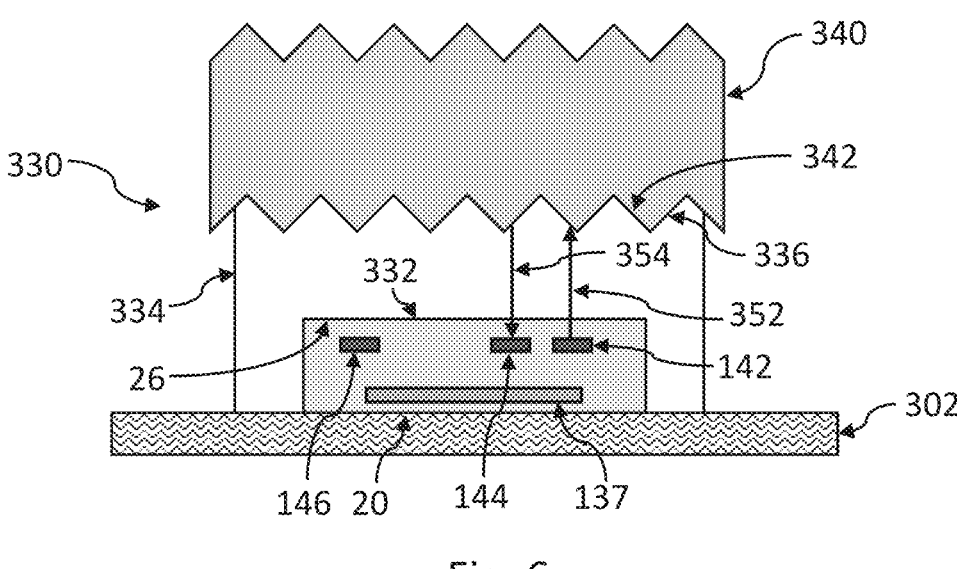

FIGS. 5 and 6 are schematic side views of an ultrasound absorption sensor module 330. The ultrasound absorption sensor module can be configured as a tactile-sensing system as explained below. The ultrasound absorption sensor module 330 includes an ultrasonic transducer device 20 and a deformable member 334 mechanically coupled to ultrasonic transducer device 20. For example, the deformable member 334 includes rubber or plastic. The ultrasonic transducer device 20 is similar to that shown in FIG. 4. In the example shown, the ultrasonic transducer device 20 is a packaged integrated circuit (IC), mounted to a circuit substrate 302. In the example shown, the deformable member 334 can be molded on the circuit substrate 302 to encapsulate the ultrasonic transducer IC 20. In the example shown, the deformable member 334 has an inner surface 332 in contact with the ultrasonic transducer device 20 and an outer surface 336 opposite the inner surface 332. In the example shown, the deformable member 334 extends between the outer surface 336 and the ultrasonic transducer device 20.

FIGS. 5 and 6 show an external object 340. In FIG. 5, the external object 340 is not in contact with the deformable member 334. The ultrasonic transmitter 142 is configured to transmit ultrasound signals (transmitted ultrasound signals). At least a portion of the transmitted ultrasound signals exits the ultrasonic transducer device 20 through its ultrasound transmission surface 26 and propagates towards the outer surface 336. For simplicity, the transmitted ultrasound signals are represented as arrow 352 pointing to the outer surface 336 even though some of the transmitted ultrasound signals may not travel towards the outer surface 336. In the example shown in FIG. 5, a relatively large fraction of the transmitted ultrasound signals 352 is reflected at the material-to-air interface (outer surface 336). Some of the reflected ultrasound signals then propagate towards the ultrasonic receivers 144. The ultrasound signals that are received by the ultrasonic receivers 144 are referred to as received ultrasound signals (shown as an arrow 354 pointing towards the ultrasonic receiver 144).

In FIG. 6, the external object 340 is impacting and/or contacting the outer surface 336: a surface 342 of the external object 340 is in contact with the outer surface 336 of the deformable member 334. The deformable member 334 is configured to conform to a contour of the external object that impacts and/or contacts the outer surface of the deformable member. There is a corresponding reduction in the reflection of ultrasound signals at outer surface 336. A first fraction $f_1$ of transmitted ultrasound signals 352 is absorbed by the external object impacting and/or contacting the outer surface. A second fraction $f_1$ of the transmitted ultrasound signals is received by the ultrasonic receiver(s) (received ultrasound signals). This second fraction $f_1$ is $1-f_1$ or less.

The ultrasound absorption sensor module 330 additionally includes a signal processor 137 electronically coupled to the ultrasonic transducer(s) 142, 144. In the example shown, the signal processor 137 is housed in the ultrasonic transducer device 20. Alternatively, the signal processor can be implemented as a separate IC and mounted on the circuit substrate 302. The signal processor 137 is configured to obtain ultrasound absorption data, in accordance with the transmitted ultrasound signals and the received ultrasound signals. For example, the signal processor can be configured to calculate the ratios of the magnitudes of the transmitted ultrasound signals and the received ultrasound signals. Such ultrasound absorption data can quantify the absorption of the transmitted ultrasound signals by the external object.

The material characteristics (including acoustic impedance, for example) of the external object determine the absorption of ultrasound signals by the external object. Accordingly, an ultrasound absorption sensor module 330 can be configured as a tactile-sensing system (e.g., 214, 216, 248). A tactile-sensing system can include an ultrasound absorption sensor module 330, configured to be positioned at a tactile edge. Additionally, the signal processor 137 can be configured to obtain at least one at least one tactile-related data from the ultrasound absorption data. The ultrasound absorption sensor module 330 can be configured to be mounted to a robot. The signal processor can be configured to obtain ultrasound absorption data before, during, and after impact. The signal processor can be configured to obtain tactile-related data from the ultrasound absorption data. For example, tactile-related data can include data relating to a material characteristic of the external object.

Figure 7:
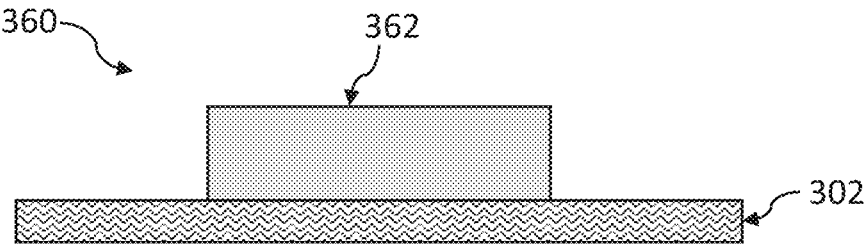
FIG. 7 is a schematic side view of an impact-sensing system.
Figure 8:
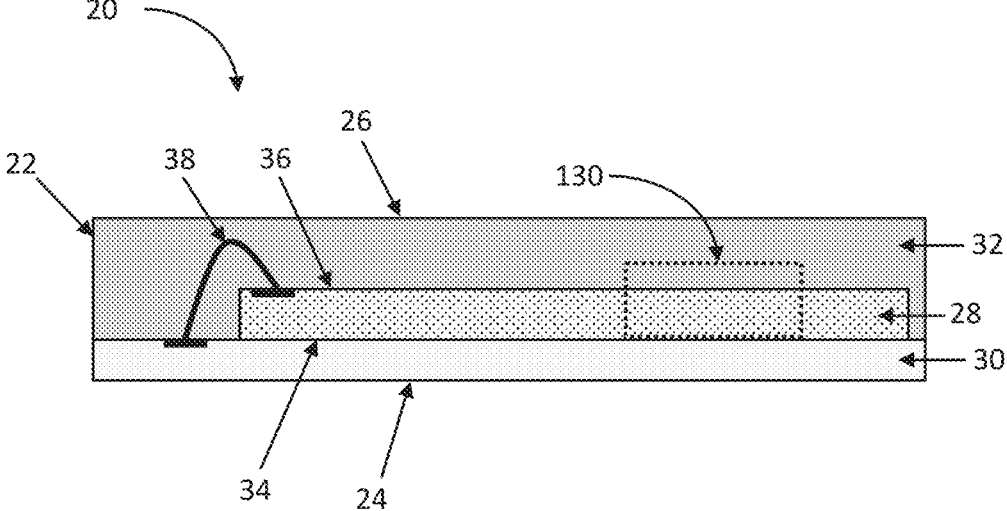
FIG. 8 is a schematic cross-sectional view of a transducer device.

An example of an ultrasonic transducer device is shown in greater detail in FIG. 8. In this case, the ultrasonic transducer device is a micromechanical systems (MEMS) device including piezoelectric micromechanical ultrasonic transducers (PMUTs) and piezoelectric force-measuring elements (PMFEs). An ultrasonic transducer can also be implemented using bulk ultrasonic transducers. One advantage of MEMS technology is that PMUTs and PMFEs can be integrated into one MEMS wafer, although the PMFEs are optional in an ultrasonic transducer device. The PMFEs can be configured to enable impact-sensing functionalities. A transducer device that includes PMFEs is an example of a force-measuring device. FIG. 7 is a schematic side view of an impact-sensing system 360. The impact-sensing system 360 includes a force-measuring device 362. In the example shown, the force-measuring device 362 is a packaged integrated circuit (IC), mounted to a circuit substrate 302. A signal processor is preferably electronically coupled to the PMFE. For example, the signal processor can reside in the force-measuring device IC. In some impact-sensing systems, the force-measuring device can be configured to be mounted to a robot. In impact-sensing systems, the force-measuring device is preferably positioned near an impact region. The signal processor is configured to obtain impact data in accordance with mechanical deformation of the PMFE resulting from an external object impacting and/or contacting the impact region. Examples of impact data are (1) time-varying impact force, (2) timing of impact, (3) magnitude of impact, (4) frequency of impact, and (5) rigidity of the external object.

FIG. 8 is a cross-sectional view of the ultrasonic transducer device 20. Device 20 is shown encased in a package 22, with an ultrasound transmission surface (top surface) 26 and electrical interconnection surface (bottom surface) 24. The ultrasonic transducer device 20 includes a package substrate 30, semiconductor portion (chip) 28 mounted to the package substrate 30, and an encapsulating adhesive 32, such as an epoxy adhesive. After the semiconductor die 28 is mounted to the package substrate 30, wire bond connections 38 are formed between the die 28 and the package substrate 30. Then the entire assembly including the die 28 and the package substrate 30 are molded (encapsulated) in an epoxy adhesive 32. It is preferable that the ultrasonic transducer device 20 have lateral dimensions no greater than 10 mm by 10 mm. The wire bond connection is formed between the top surface 36 of the semiconductor die 28 and the package substrate 30. Alternatively, electrical interconnections can be formed between the bottom surface 34 of the semiconductor die 28 and the package substrate. The semiconductor die 28 consists of an application-specific integrated circuit (ASIC) portion and a micro-electro-mechanical systems (MEMS) portion. A selected portion 130 of the semiconductor die 28 is shown in cross-section in FIG. 9.

Figure 9:
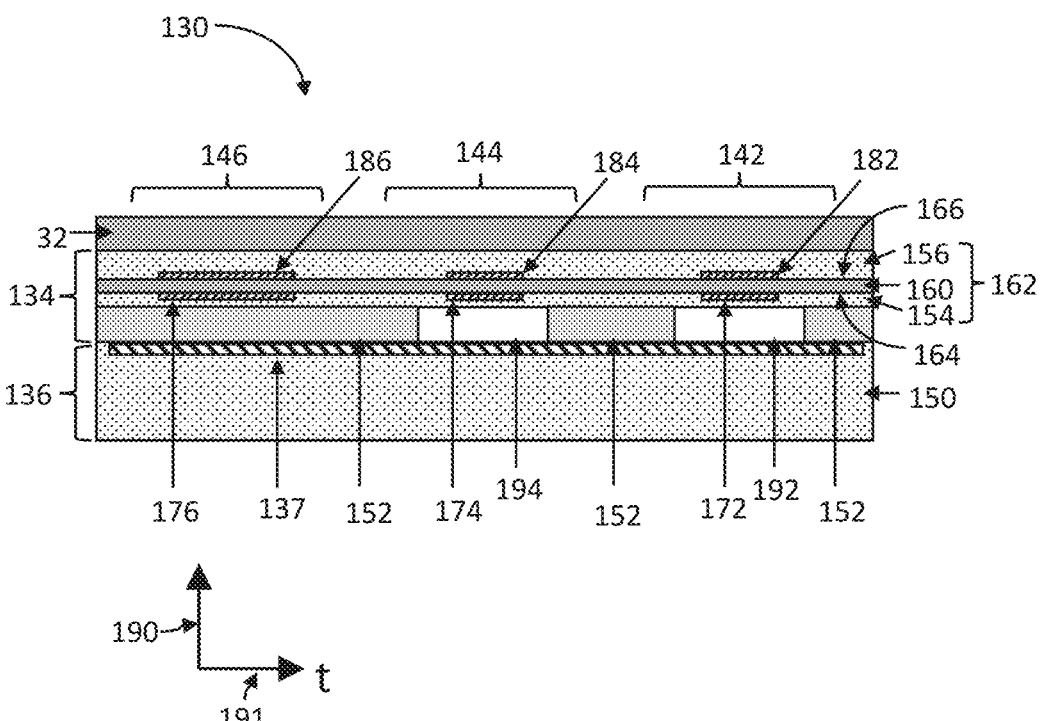
FIG. 9 is a schematic cross-sectional view of a certain portion of the transducer device of FIG. 8.

FIG. 9 is a schematic cross-sectional view of a portion 130 of the ultrasonic transducer device of FIG. 8. The semiconductor die 28 includes a MEMS portion 134 and an ASIC portion 136. Between the ASIC portion 136 and the MEMS portion 134, the MEMS portion 134 is closer to the ultrasound transmission surface 26 and the ASIC portion 136 is closer to the electrical interconnection surface 24. The ASIC portion 136 consists of a semiconductor substrate 150 and signal processor 137 thereon. Typically, the semiconductor substrate is a silicon substrate, but other semiconductor substrates such as silicon-on-insulator (SOI) substrates can also be used.

The MEMS portion 134 includes a PMUT transmitter 142, a PMUT receiver 144, and a PMFE 146. The PMFE 146 is not necessary for an ultrasonic transducer device. However, the PMFEs can provide additional functionality and can be made using the same MEMS manufacturing steps as the PMUT transmitters and receivers. The MEMS portion 134 includes a thin-film piezoelectric stack 162 overlying the semiconductor substrate 150. The thin-film piezoelectric stack 162 includes a piezoelectric layer 160, which is a layer exhibiting the piezoelectric effect. Suitable materials for the piezoelectric layer 160 are aluminum nitride, scandium-doped aluminum nitride, polyvinylidene fluoride (PVDF), lead zirconate titanate (PZT), $K_xNa_{1-x}NbO_3$ (KNN), quartz, zinc oxide, and lithium niobate, for example. For example, the piezoelectric layer is a layer of aluminum nitride having a thickness of approximately 1 $\mu$m. The piezoelectric layer 160 has a top major surface 166 and a bottom major surface 164 opposite the top major surface 166. In the example shown, the thin-film piezoelectric stack 162 additionally includes a top mechanical layer 156, attached to or adjacent to (coupled to) top major surface 166, and a bottom mechanical layer 154, attached to or adjacent to (coupled to) bottom major surface 164. In the example shown, the thickness of the top mechanical layer 156 is greater than the thickness of the bottom mechanical layer 154. In other examples, the thickness of the top mechanical layer 156 can be smaller than the thickness of the bottom mechanical layer 154. Suitable materials for the mechanical layer(s) are silicon, silicon oxide, silicon nitride, and aluminum nitride, for example. Suitable materials for the mechanical layer(s) can also be a material that is included in the piezoelectric layer 160, which in this case is aluminum nitride. In the example shown, the top mechanical layer and the bottom mechanical layer contain the same material. In other examples, the top mechanical layer and the bottom mechanical layer are of different materials. In other examples, one of the top mechanical layer and the bottom mechanical layer can be omitted. When coupled to the elastic member 304 (FIG. 4) or the deformable member 334 (FIGS. 5, 6), the ultrasonic transducer device 20 is preferably oriented such that the piezoelectric layer 160 faces toward the cover layer 306 or the outer surface 336. For example, the ultrasonic transducer device 20 is oriented such that the piezoelectric layer 160 and the cover layer 306 or the outer surface 336 are approximately parallel.

For ease of discussion, only one of each of the PMUT transmitters, PMUT receivers, and PMFEs is shown in FIG. 9. However, a transducer device can contain a plurality of PMUT transmitters, PMUT receivers, and PMFEs. The PMUT transmitters, the PMUT receivers, and the PMFEs are located along respective lateral positions along the thin-film piezoelectric stack 162. Each PMUT transmitter, PMUT receiver, and PMFE includes a respective portion of the thin-film piezoelectric stack.

Each of the PMUTs is configured as a transmitter (142) or a receiver (144). Each PMUT (142, 144) includes a cavity (192, 194) and a respective portion of the thin-film piezo-electric stack 162 overlying the cavity (192, 194). The cavities are laterally bounded by an anchor layer 152 which supports the thin-film piezoelectric stack. Suitable materials for the anchor layer 152 are silicon, silicon nitride, and silicon oxide, for example. Suitable materials for the anchor layer 152 can also be a material that is included in the piezoelectric layer 160, which in this case is aluminum nitride. Each PMUT (142, 144) includes a first PMUT electrode (172, 174) positioned on a first side (bottom surface) 164 of the piezoelectric layer 160 and a second PMUT electrode (182, 184) positioned on a second side (top surface) 166 opposite the first side. In each PMUT (142, 144), the first PMUT electrode (172, 174), the second PMUT electrode (182, 184), and the piezoelectric layer 160 between them constitute a piezoelectric capacitor. The first PMUT electrodes (172, 174) and the second PMUT elec-trodes (182, 184) are coupled to the signal processor 137. The cavities (192, 194) are positioned between the thin-film piezoelectric stack 162 and the semiconductor substrate 150. In the example shown, the ultrasonic transducer device 20 is in the form of an encapsulated package 22. The cavities 192, 194 are preferably under low pressure (pressure lower than atmospheric pressure or in vacuum) and remain so because of the package 22.

Each PMFE 146 includes a respective portion of the thin-film piezoelectric stack 162. Each PMFE 146 includes a first PMFE electrode 176 positioned on a first side (bottom surface) 164 of the piezoelectric layer 160 and a second PMFE electrode 186 positioned on a second side (top surface) 166 opposite the first side. In each PMFE 146, the first PMFE electrode 176, the second PMFE electrode 186, and the piezoelectric layer 160 between them constitute a piezoelectric capacitor. The PMFEs are coupled to the signal processor 137. In the example shown, the PMFE is not overlying any cavity.

The signal processor 137 is operated to generate and apply a time-varying voltage signal $V_{Tx}(t)$ between the PMUT electrodes (172, 182) of the PMUT transmitter 142. If the time-varying voltage signal oscillates between the first transmitter voltage and the second transmitter voltage at a certain frequency, the portion of the piezoelectric stack 162 oscillates between the first transmitter state and the second transmitter state at that frequency. As a result, the PMUT transmitter generates (transmits), upon application of the time-varying voltage signal, ultrasound signals propagating along the normal direction 190. Because of the presence of the cavity 192 at a low pressure, a relatively small fraction of the generated ultrasound energy is transmitted downward toward the cavity 192, and a relatively large fraction of the generated ultrasound energy is transmitted upward away from the cavity 192. The PMUT transmitters are configured to transmit ultrasound signals of a frequency in a range of 0.1 MHz to 25 MHz.

If ultrasound signals are incident on the PMUT receiver 144 along the normal direction 190 causing the portion of the piezoelectric stack 162 to oscillate between the first receiver state and the second receiver state, a time-varying voltage signal $V_{Rx}(t)$ oscillating between the first receiver voltage and the second receiver voltage is generated between the PMUT electrodes (174, 184). The time-varying voltage signal is amplified and processed by the signal processor 137.

In operation, the PMUT transmitter 142 is configured to transmit, upon application of voltage signals between the PMUT transmitter electrodes (172, 182), ultrasound signals of a first frequency $F_1$, in longitudinal mode(s) propagating along a normal direction 190 approximately normal to the piezoelectric layer 160 away from the cavity 192. Upon application of the voltage signals, the respective portion of the piezoelectric stack overlying the cavity 192 (of the PMUT transmitter 142) oscillates with a first frequency $F_1$ between a first transmitter state and a second transmitter state to generate ultrasound signals of the first frequency $F_1$. The ultrasound signals propagate towards the cover layer 306 (FIG. 4) or the outer surface 336 (FIGS. 5, 6) depending on whether the ultrasonic transducer device is incorporated into an ultrasound TOF sensor module or an ultrasound absorption sensor module. Some fraction of the ultrasound signals transmitted by the PMUT transmitter 142 returns to the PMUT receiver 144 as an echo ultrasound signal. The PMUT receiver 144 is configured to output, in response to ultrasound signals of the first frequency $F_1$ arriving along the normal direction, voltage signals between the PMUT receiver electrodes (174, 184). In response to ultrasound signals of the first frequency $F_1$ arriving along the normal direction, the portion of the thin-film piezoelectric stack 162 overlying the cavity oscillates at the first frequency $F_1$.

A portion 130 of the transducer device 20 containing a PMFE 146 is shown in cross section in FIG. 9. Also shown is the ASIC portion 136 that is under the PMFE 146 and the encapsulating adhesive 32 that is above the PMFE 146. FIG. 9 shows the PMFE in a quiescent state, in which there is no flexing of the piezoelectric stack 162. In the quiescent state, there is no voltage generated between the PMFE electrodes (176, 186).

When there is an impact force that is transmitted to the transducer device 20 (hence, to the PMFEs 146), a time-dependent oscillatory deformation of the piezoelectric layer 160 is induced at the PMFE 146. The oscillatory deforma-tion can include a deflection of the piezoelectric layer 160 at the PMFE 146. The oscillatory deformation can include lateral deformation (compression and expansion along the lateral direction 191 approximately parallel to piezoelectric layer 160), normal deformation (compression and expansion along the normal direction 190 approximately normal to the piezoelectric layer 160), and shear deformation. As a result, time-varying electrical charges are generated at each PMFE (146) between the respective PMFE electrodes (176, 186). These time-varying electrical charges are detectable as time-varying voltage signals. The signal processor 137 amplifies and processes these time-varying voltage signals. In opera-tion, PMFE 146 is configured to output voltage signals between the PMFE electrodes (176, 186) in accordance with a time-varying piezoelectric strain at the respective portion of the piezoelectric layer between the PMFE electrodes (176, 186) resulting from the mechanical deformation.

Figure 10:
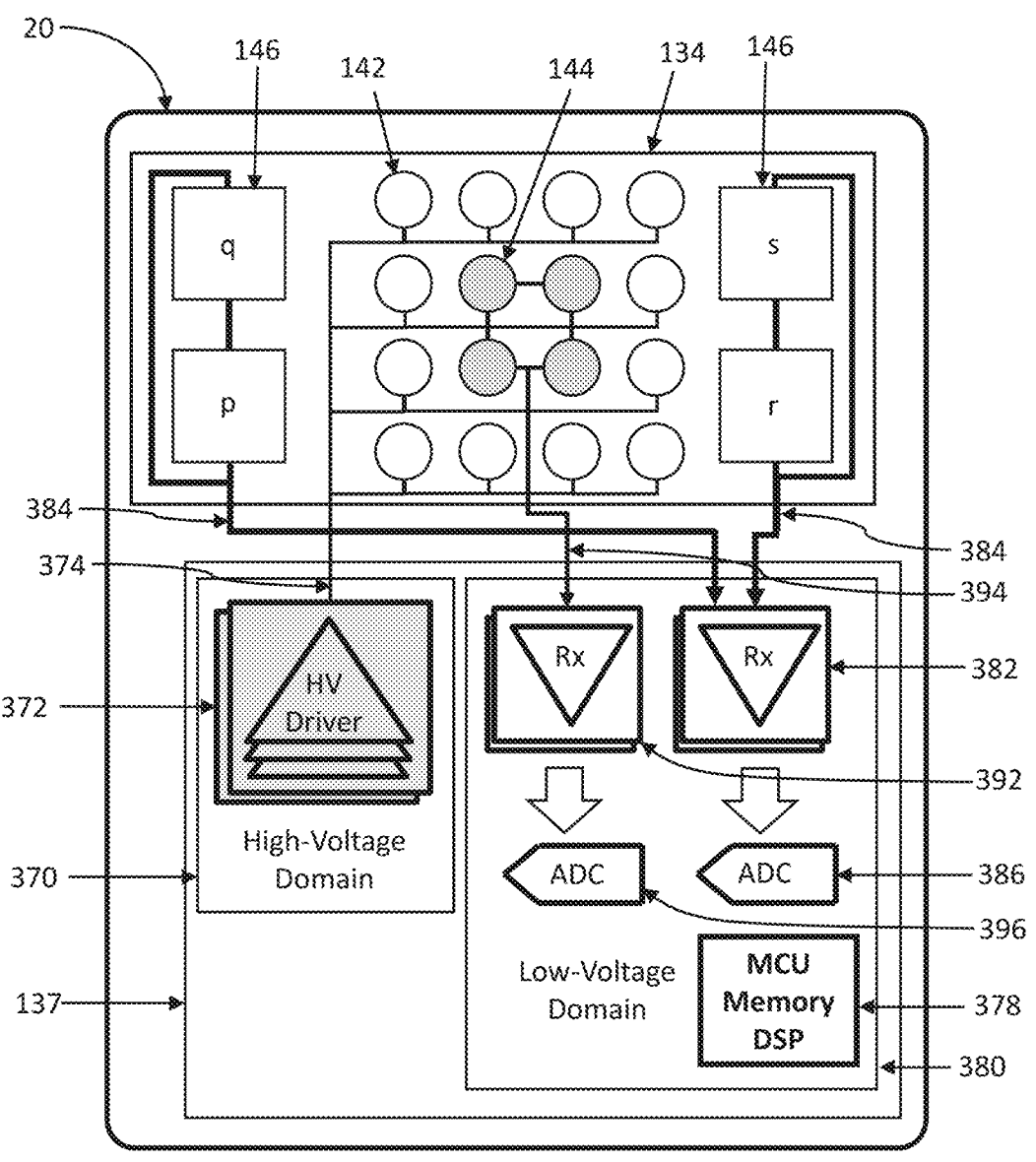
FIG. 10 is an electronics block diagram of a transducer device.

FIG. 10 is an electronics block diagram of the ultrasonic transducer device 20, including a MEMS portion 134 and signal processor 137. The MEMS portion includes PMUT transmitters 142, PMUT receivers 144, and PMFEs 146. Signal processor 137 includes a high-voltage domain 370 and a low-voltage domain 380. The high-voltage domain can operate at higher voltages required for driving the PMUT transmitters. The high-voltage domain includes high-voltage transceiver circuitry 372, including high-voltage drivers. The high-voltage transceiver circuitry 372 is connected to the first PMUT electrodes and the second PMUT electrodes of the PMUT transmitters, via electrical interconnections (wiring) 374. The high-voltage transceiver is configured to output voltage pulses of 5 V or greater, depending on the requirements of the PMUT transmitters.

The low-voltage domain 380 includes amplifiers (382, 392) and analog-to-digital converters (ADCs) (386, 396). The processing circuit blocks 378 are also contained in the low-voltage domain 380. Voltage signals output by the PMUT receivers 144 (represented by gray circles) reach amplifiers 392 via electrical interconnections (wiring) 394 and get amplified by the amplifiers 392. The amplified voltage signals are sent to ADC 396 to be converted to digital signals which can be processed or stored by processing circuit blocks 378. Similarly, voltage signals output by PMFEs 146 reach amplifiers 382 via electrical interconnections (wiring) 384 and get amplified by the amplifiers 382. These amplified voltage signals are sent to ADC 386 to be converted to digital signals which can be processed or stored by processing circuit blocks 378. The processing circuit blocks 288 can include microcontrollers (MCUs), memories, and digital signal processors (DSPs), for example. The wiring (374, 384, 394) traverses the semiconductor substrate, which contains the signal processor 137, and the MEMS portion 134, which contains the PMFEs 146, the PMUT transmitters 142, and the PMUT receivers 144.

In the example shown (FIG. 10), the piezoelectric capacitors constituting the PMUT receivers 144 are connected to each other in parallel. Since the capacitances of these PMUT receivers are added together, this arrangement of PMUT receivers is less sensitive to the effects of parasitic capacitance. Accordingly, there is a unified voltage signal transmitted from the PMUT receivers 144 to the amplifiers 392. In the example shown, the piezoelectric capacitors constituting the PMUT transmitters 142 are connected in parallel. Accordingly, there is one set of time-varying signal transmitted from the high-voltage transceiver circuitry 372 to the PMUT transmitters 142. The PMFEs 146 are grouped into two sets (p and q on the left side, r and s on the right side), and the PMFEs in each set are connected to each other in series. Accordingly, there are two sets of PMFE signals transmitted from the PMFEs 146 to the amplifiers 382.

A tactile-sensing system can be implemented using an ultrasound TOF sensor module or an ultrasound absorption sensor module. A tactile-sensing system can include an ultrasound TOF sensor module configured to be positioned at a tactile edge. The signal processor is configured to obtain at least one tactile-related data from the ultrasound time-of-flight data when the external object impacts and/or contacts the cover layer. Examples of tactile-related data are (1) a material characteristic of the external object and (2) rigidity of the external object.

Alternatively, a tactile-sensing system can include an ultrasound absorption sensor module configured to be positioned at a tactile edge. The signal processor is configured to obtain at least one-tactile related data from the ultrasound absorption data when the external object impacts and/or contacts the outer surface. An example of a tactile-related data is a material characteristic of the external object.

An ultrasonic transducer device of a tactile-sensing system can optionally include PMFEs. The signal processor is electronically coupled to the PMFEs. The signal processor is configured to obtain impact data in accordance with mechanical deformation of the PMFE resulting from the impact and/or contact (e.g., the external object impacting and/or contacting the cover layer 306 (FIG. 4) or the outer surface 336 (FIGS. 5, 6)). Examples of impact data are (1) time-varying impact force, (2) timing of impact, (3) magnitude of impact, (4) frequency of impact, and (5) rigidity of the external object.

Figure 11:
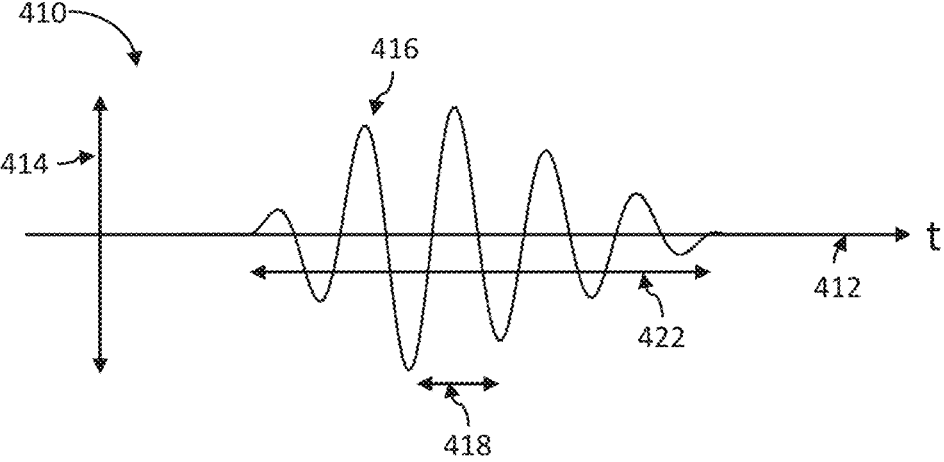
FIG. 11 shows a graphical plot of an ultrasound waveform transmitted by a PMUT transmitter.

FIG. 11 is a schematic graphical plot 410 of an ultrasound waveform 416, transmitted by a PMUT transmitter. Graphical plot 410 has a horizontal axis 412 showing time and a vertical axis 414 showing an amplitude of the ultrasound signal. In the example shown, the ultrasound waveform has a duration 422 and an oscillation period 418. Typically, the PMUT transmitters are configured to transmit ultrasound signals of a frequency in a range of 0.1 MHz to 25 MHz, corresponding to oscillation periods 418 ranging between 10 $\mu$s and 40 ns.

Figure 12:
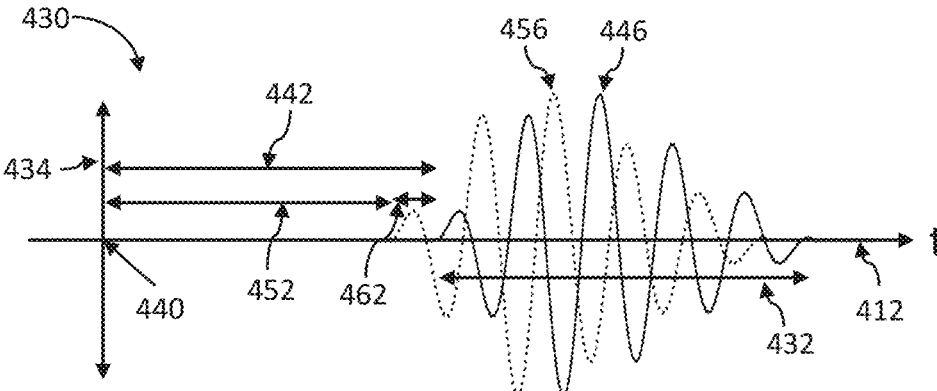
FIG. 12 is a graphical plot of two echo ultrasound waveforms that vary in ultrasound propagation distance.

FIG. 12 is a schematic graphical plot 430 of ultrasound waveforms 446 (solid line) and 456 (dotted line) received by a PMUT receiver in an ultrasound TOF sensor module. For both waveforms, the PMUT transmitter transmitted ultrasound signals at time $T=T_0$ (shown as 440). The ultrasound signals transmitted by the PMUT transmitter were reflected by the cover layer and the reflected ultrasound signals are received by the PMUT receiver. The PMUT receiver receives waveform 456 earlier than waveform 446. Waveform 446 corresponds to a first instance in which the elastic member is not compressed (is in its quiescent state). Waveform 456 corresponds to a second instance in which the elastic member is compressed, in response to an external object impacting and/or contacting the cover layer. Accordingly, the ultrasound propagation distance is shorter in the second instance than in the first instance. Time differences $\Delta T$ are differences between times of transmission of transmitted ultrasound signals by the ultrasonic transmitter(s) and times of receipt of reflected ultrasound signals by the ultrasonic receiver(s). In the first instance (waveform 446), the time difference $\Delta T$ is shown by line 442. In the second instance (waveform 456), the time difference $\Delta T$ is shown by line 452 (shorter than line 442 by time duration represented by line 462). The time differences vary in accordance with the ultrasound propagation distance. Time-of-flight data obtained by the signal processor can be any data that indicates time differences between times of transmission of transmitted ultrasound signals by the ultrasonic transmitter(s) and times of receipt of reflected ultrasound signals by the ultrasonic receiver(s). For example, the time-of-flight data can include the time durations of lines 442 and 452. Additionally, the time-of-flight data can include other data that can be derived from processing and comparison of waveforms 446, 456.

Figure 13:
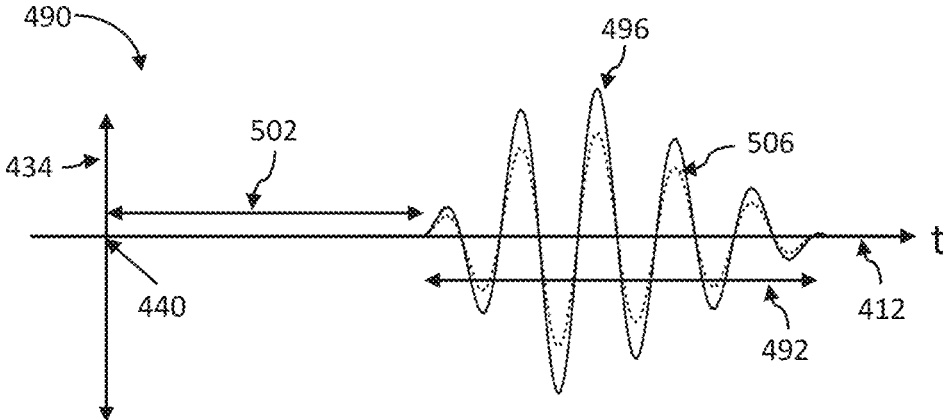
FIG. 13 is a graphical plot of two echo ultrasound waveforms that vary in ultrasound absorption.

FIG. 13 is a schematic graphical plot 490 of ultrasound waveforms 496 (solid line) and 506 (dotted line) received by a PMUT receiver in an ultrasound absorption sensor module. For both waveforms, the PMUT transmitter transmitted ultrasound signals at time $T=T_0$ (shown as 440). Some of the ultrasound signals transmitted by the PMUT transmitter are received by the PMUT receiver. As received by the PMUT receiver, waveform 506 has a smaller amplitude than waveform 496. Waveform 496 corresponds to a first instance in which there is no external object impacting and/or contacting the outer surface. Waveform 506 corresponds to a second instance in which some of the transmitted ultrasound signals are absorbed by an external object impacting and/or contacting the outer surface of the deformable member. Accordingly, the ultrasound signals have a smaller amplitude in the second instance than in the first instance. The signal processor is configured to obtain ultrasound absorption data in accordance with the transmitted ultrasound signals and the received ultrasound signals. Such ultrasound absorption data can quantify the absorption of the transmitted ultrasound signals by the external object. For example, the signal processor can be configured to calculate the ratios of the magnitudes of the transmitted ultrasound signals and the received ultrasound signals. This ratio varies depending on whether there is an external object that is impacting and/or contacting the outer surface and depending on the material properties of the external object.

Figure 14:
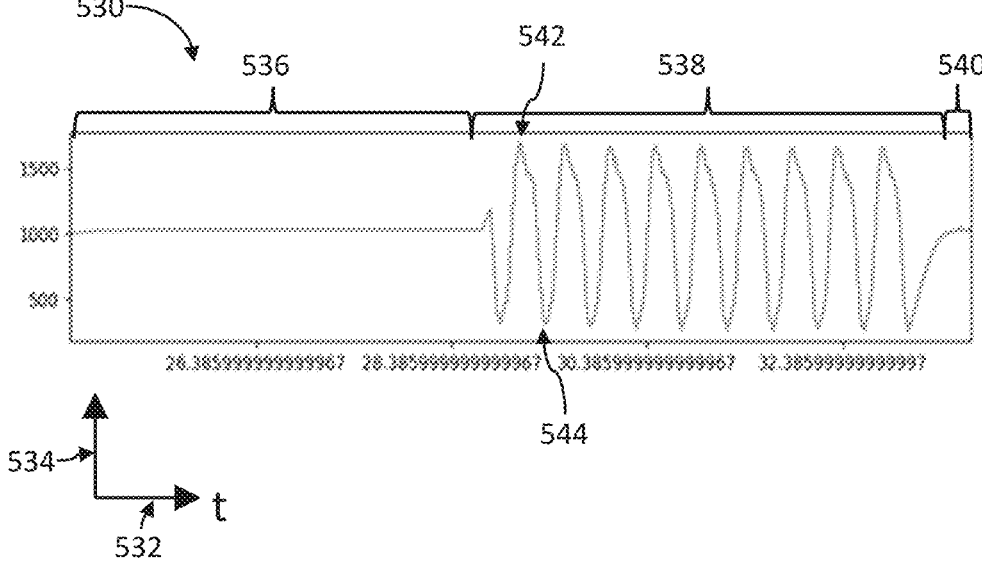
FIG. 14 is a graphical plot of PMFE data in response to a repetitive impact.

FIG. 14 shows a graphical plot 530 of illustrative PMFE data during a period of repetitive impact. Graphical plot 530 has a horizontal axis 532 showing time t, and a vertical axis 534 showing PMFE data, after amplification and analog-to-digital conversion. Graphical plot 530 includes plot sections 536, 538, and 540 (ordered sequentially). Graphical plot portions 536 and 540 show the baseline signal. Plot section 538 corresponds to repetitive impact. There is a pair of maximum PMFE data 542 and a minimum PMFE data 544 (occurring after 442) corresponding to one repetition of the impact event. First, the PMFE(s) undergo a first deformation resulting in a first PMFE signal, and then the PMFE(s) undergo a second deformation resulting in a second PMFE signal. In this case, the first and second deformations are in opposite directions and the first and second PMFE signals are of opposite polarities relative to the baseline signal. Impact data that can be obtained by the signal processor include: (1) time-varying impact force, (2) timing of impact, (3) magnitude of impact, (4) frequency of impact, and (5) rigidity of the external object.

Figure 15:
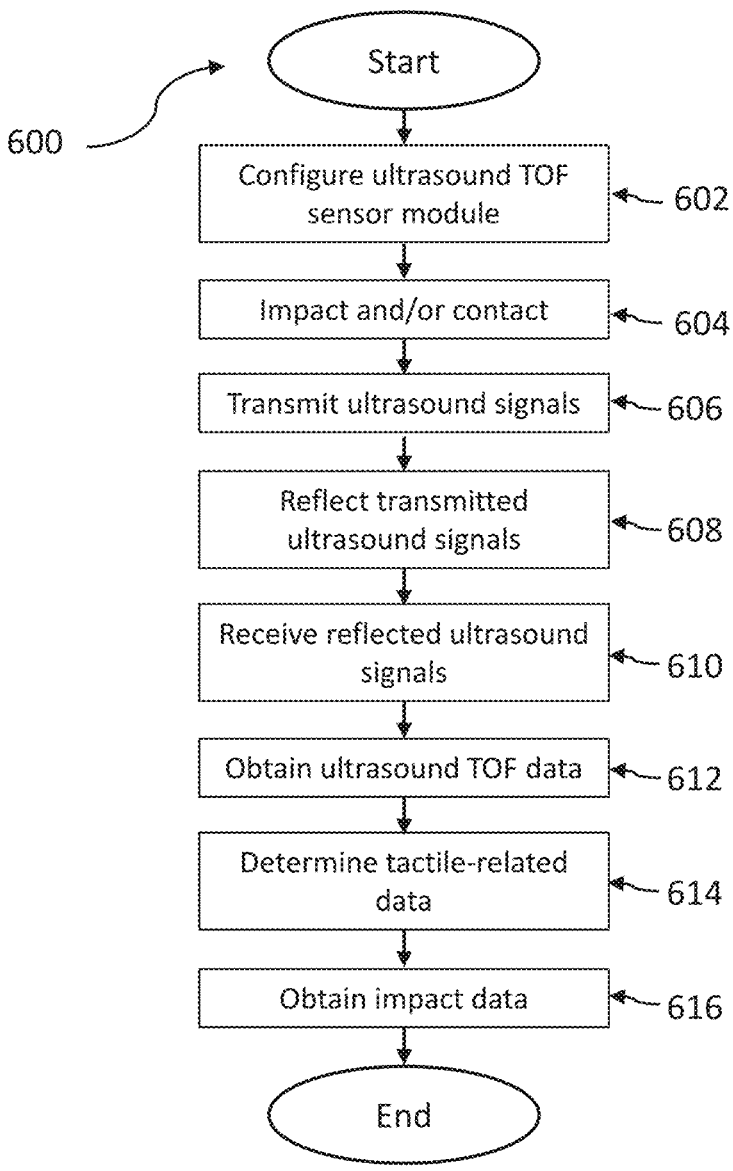
FIG. 15 is a flow diagram of a tactile-sensing method using an ultrasound time-of-flight sensor module.

FIG. 15 is a flow diagram of a tactile-sensing method 600, using an ultrasound time-of-flight sensor module. Method 600 includes steps 602, 604, 606, 608, 610, 612, 614, and 616. Step 616 is optional. Step 602 includes configuring an ultrasound time-of-flight sensor module positioned at a tactile edge. The ultrasound time-of-flight sensor module includes (1) an ultrasonic transducer device including at least one ultrasonic transducer (each ultrasonic transducer is configured as an ultrasonic transmitter and/or an ultrasonic receiver), (2) a cover layer, and (3) an elastic member interposed between the ultrasonic transducer device and the cover layer and mechanically coupled to the cover layer and to the ultrasonic transducer device. Step 604 includes moving the tactile edge towards an external object and/or moving the external object towards the tactile edge such that the external object impacts and/or contacts the cover layer, and the elastic member undergoes reversible compression. An ultrasound propagation distance between the ultrasonic transducer and the cover layer varies in accordance with the compression.

Step 606 includes transmitting, by the ultrasonic transmitter(s), ultrasound signals (transmitted ultrasound signals) towards the cover layer. Step 608 includes reflecting, by the cover layer, a fraction f of ultrasound signals incident thereon (reflected ultrasound signals). Step 610 includes receiving, by the ultrasonic receiver(s), the reflected ultrasound signals. Step 612 includes obtaining, by a signal processor, time-of-flight data at least in part from the reflected ultrasound signals. The time-of-flight data indicate time differences between times of transmission of transmitted ultrasound signals by the ultrasonic transmitter(s) and times of receipt of reflected ultrasound signals by the ultrasonic receiver(s). The time differences vary in accordance with the ultrasound propagation distance. Step 614 includes determining, by the signal processor, at least one tactile-related data of the external object from the time-of-flight data. Examples of tactile-related data are (1) a material characteristic of the external object or (2) rigidity of the external object. Step 616 includes obtaining, by the signal processor, impact data in accordance with mechanical deformation of the PMFE resulting from the impact and/or contact. Step 616 is an optional step. Step 634 is an optional step. In order to carry out step 616, step 602 additionally includes configuring a PMFE. Accordingly, the signal processor is electronically coupled to the PMFE. Examples of impact data are: (1) time-varying impact force, (2) timing of impact, (3) magnitude of impact, (4) frequency of impact, and (5) rigidity of the external object. By concurrently obtaining both tactile-related and impact data, properties of the external object can be determined with greater confidence.

Figure 16:
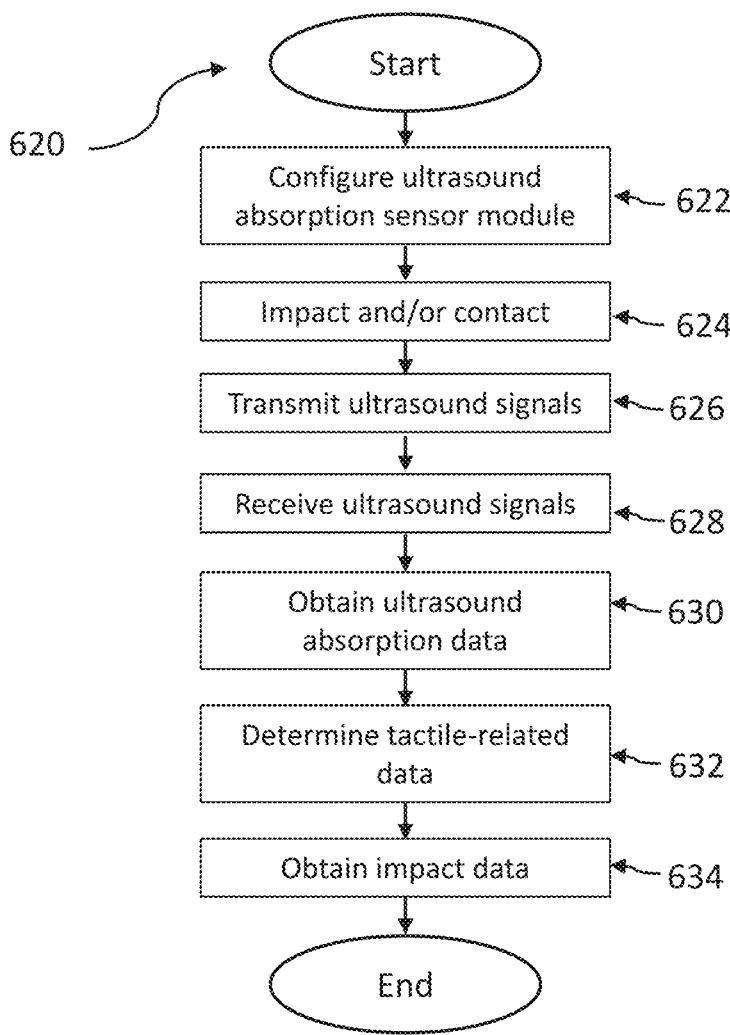
FIG. 16 is a flow diagram of a tactile-sensing method using an ultrasound absorption sensor module.

FIG. 16 is a flow diagram of a tactile-sensing method 620, using an ultrasound absorption sensor module. Method 620 includes steps 622, 624, 626, 628, 630, 632, and 634. Step 622 includes configuring an ultrasound absorption sensor module positioned at a tactile edge. The ultrasound absorption sensor module includes (1) an ultrasonic transducer device including at least one ultrasonic transducer (each ultrasonic transducer is configured as an ultrasonic transmitter and/or an ultrasonic receiver), and (2) a deformable member mechanically coupled to the ultrasonic transducer device and configured to conform to a contour of an external object that impacts and/or contacts an outer surface of the deformable member. Step 624 includes moving the tactile edge towards the external object and/or moving the external object towards the tactile edge such that the external object impacts and/or contacts the outer surface of the deformable member, and the deformable member conforms to the contour of the external object.

Step 626 includes transmitting, by the ultrasonic transmitter(s), ultrasound signals (transmitted ultrasound signals) towards the outer surface. A first fraction $f_1$ of transmitted ultrasound signals is absorbed by the external object impacting and/or contacting the outer surface. Step 628 includes receiving, by the ultrasonic receiver(s), a second fraction $f_1$ of the transmitted ultrasound signals (received ultrasound signals). The second fraction $f_1$ is $1-f_1$ or less. Step 630 includes obtaining, by a signal processor, ultrasound absorption data in accordance with the transmitted ultrasound signals and the received ultrasound signals. Step 632 includes determining, by the signal processor, at least one tactile-related data from the ultrasound absorption data. An example of tactile-related data is a material characteristic of the external object. Step 634 includes obtaining, by the signal processor, impact data in accordance with mechanical deformation of the PMFE resulting from the impact and/or contact. Step 634 is an optional step. In order to carry out step 634, step 622 additionally includes configuring a PMFE. Accordingly, the signal processor is electronically coupled to the PMFE. Examples of impact data are: (1) time-varying impact force, (2) timing of impact, (3) magnitude of impact, (4) frequency of impact, and (5) rigidity of the external object. By concurrently obtaining both tactile-related and impact data, properties of the external object can be determined with greater confidence.

Figure 17:
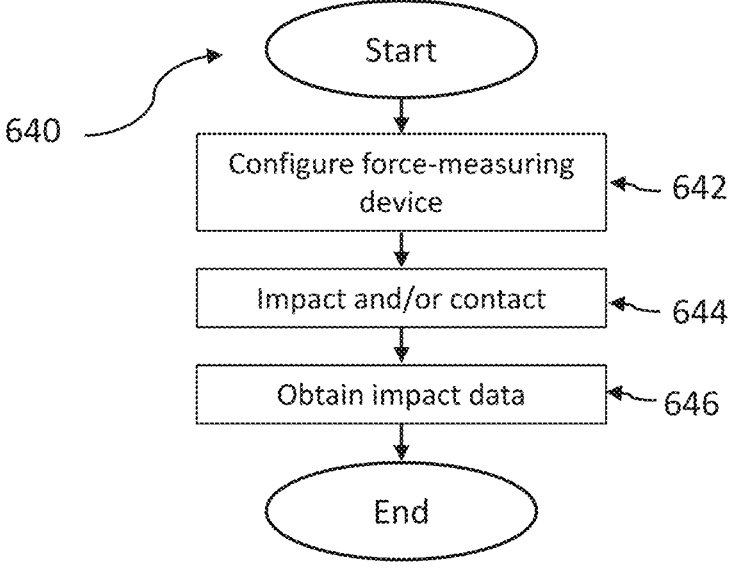
FIG. 17 is a flow diagram of an impact-sensing method.

FIG. 17 is a flow diagram of an impact-sensing method 640. Method 640 includes steps 642, 644, and 646. Step 642 includes configuring a force-measuring device positioned near an impact region. The force-measuring device includes a piezoelectric micromechanical force-measuring element (PMFE). Step 644 includes moving the impact region towards an external object and/or moving the external object towards the impact region such that the external object impacts and/or contacts the impact region. Step 646 includes obtaining, by a signal processor, impact data in accordance with mechanical deformation of the PMFE resulting from the impact. Examples of impact data are: (1) time-varying impact force, (2) timing of impact, (3) magnitude of impact, (4) frequency of impact, and/or (5) rigidity of the external object.

In the foregoing description of embodiments of modules, systems, and methods, PMFEs have been discussed as examples of force-measuring elements. Nevertheless, it is not necessary to employ PMFEs to realize the advantages of the present invention. More generally, it is possible to use piezoelectric force-measuring elements. It is not necessary that the piezoelectric force-measuring elements and the ultrasound transceivers be integrated into a single MEMS IC. It is not necessary that the ultrasound transceivers be micromechanical elements. Piezoelectric force-measuring elements that are micromechanical (e.g., fabricated by MEMS technologies) are referred to as piezoelectric micro-mechanical force-measuring elements (PMFEs). Instead of using MEMS technologies, it is also possible to fabricate piezoelectric force-measuring elements using bulk piezo-electric membranes, such as lead zirconate titanate (PZT). In either case, a signal processor could be electronically coupled to the piezoelectric force-measuring element, and the signal processor can be configured to read voltage signals from the piezoelectric force-measuring element resulting from mechanical deformation of the piezoelectric force-measuring element. Furthermore, in a tactile-sensing system, the signal processor can be configured to obtain impact data in accordance with mechanical deformation of the piezoelectric force-measuring element resulting from the impact and/or contact. More generally, it is possible to use force-measuring elements that are not necessarily piezoelec-tric force-measuring elements. Such force-measuring elements include capacitive force sensors and piezoresistive strain gauges for example. In such cases, a signal processor could be electronically coupled to the force-measuring element, and the signal processor can be configured to read signals from the force-measuring element. Furthermore, in a tactile-sensing system, the signal processor can be config-ured to obtain impact data from the force-measuring element.

What is claimed is:

1. An ultrasound time-of-flight sensor module, compris-ing:

an ultrasonic transducer device comprising at least one ultrasonic transducer, each ultrasonic transducer being configured as an ultrasonic transmitter and/or an ultra-sonic receiver;

a cover layer;

an elastic member interposed between the ultrasonic transducer device and the cover layer and mechanically coupled to the cover layer and to the ultrasonic trans-ducer device; and a signal processor electronically coupled to the ultrasonic transducer;

wherein the elastic member undergoes reversible com-pression in response to an external object impacting and/or contacting the cover layer, an ultrasound propa-gation distance between the ultrasonic transducer and the cover layer varying in accordance with the com-pression;

ultrasonic transmitter(s) are configured to transmit ultra-sound signals (transmitted ultrasound signals) towards the cover layer;

the cover layer is configured to reflect a fraction f of ultrasound signals incident thereon (reflected ultra-sound signals);

ultrasonic receiver(s) are configured to receive the reflected ultrasound signals;

the signal processor is configured to obtain time-of-flight data indicating time differences between times of trans-mission of transmitted ultrasound signals by the ultra-sonic transmitter(s) and times of receipt of reflected ultrasound signals by the ultrasonic receiver(s); and the time differences vary in accordance with the ultra-sound propagation distance.

2. The ultrasound time-of-flight sensor module of claim 1, wherein the signal processor is housed in the ultrasonic transducer device.

3. The ultrasound time-of-flight sensor module of claim 1, wherein the fraction f is at least 50%.

4. The ultrasound time-of-flight sensor module of claim 1, wherein the elastic member comprises rubber or plastic.

5. The ultrasound time-of-flight sensor module of claim 1, wherein the elastic member is more deformable than the cover layer.

6. The ultrasound time-of-flight sensor module of claim 1, wherein the cover layer comprises metal.

7. The ultrasound time-of-flight sensor module of claim 6, wherein the metal is aluminum.

8. The ultrasound time-of-flight sensor module of claim 1, wherein:

the ultrasonic transducer device additionally comprises a force-measuring element;

the signal processor is electronically coupled to the force-measuring element; and the signal processor is configured to read signals from the force-measuring element.

9. The ultrasound time-of-flight sensor module of claim 8, wherein:

the force-measuring element is a piezoelectric force-measuring element; and the signal processor is configured to read voltage signals from the piezoelectric force-measuring element result-ing from mechanical deformation of the piezoelectric force-measuring element.

10. The ultrasound time-of-flight sensor module of claim 9, wherein the force-measuring element is a piezoelectric micromechanical force-measuring element (PMFE).

11. A tactile-sensing system, comprising:

the ultrasound time-of-flight sensor module of claim 1, configured to be positioned at a tactile edge;

wherein the signal processor is configured to obtain at least one tactile-related data from the ultrasound time-of-flight data when the external object impacts and/or contacts the cover layer.

12. The tactile-sensing system of claim 11, wherein the tactile-related data is selected from (1) a material charac-teristic of the external object and (2) rigidity of the external object.

13. The tactile-sensing system of claim 11, wherein the ultrasound time-of-flight sensor module is configured to be mounted to a robot.

14. The tactile-sensing system of claim 11, additionally comprising: a force-measuring element;

wherein the signal processor is electronically coupled to the force-measuring element; and the signal processor is configured to obtain impact data from the force-measuring element.

15. The tactile-sensing system of claim 14, wherein:

the force-measuring element is a piezoelectric force-measuring element; and the signal processor is configured to obtain impact data in accordance with mechanical deformation of the piezoelectric force-measuring element resulting from the impact and/or contact.

16. The tactile-sensing system of claim 15, wherein the force-measuring element is a piezoelectric micromechanical force-measuring element (PMFE).

17. The tactile-sensing system of claim 14, wherein the impact data is selected from: (1) time-varying impact force, (2) timing of impact, (3) magnitude of impact, (4) frequency of impact, and (5) rigidity of the external object.

18. A tactile-sensing method, comprising the steps of:

configuring an ultrasound time-of-flight sensor module positioned at a tactile edge, the ultrasound time-of-flight sensor module comprising (1) an ultrasonic transducer device comprising at least one ultrasonic transducer, each ultrasonic transducer being configured as an ultrasonic transmitter and/or an ultrasonic receiver, (2) a cover layer, and (3) an elastic member interposed between the ultrasonic transducer device and the cover layer and mechanically coupled to the cover layer and to the ultrasonic transducer device;

moving the tactile edge towards an external object and/or moving the external object towards the tactile edge such that the external object impacts and/or contacts the cover layer and the elastic member undergoes reversible compression, an ultrasound propagation distance between the ultrasonic transducer and the cover layer varying in accordance with the compression;

transmitting, by the ultrasonic transmitter(s), ultrasound signals (transmitted ultrasound signals) towards the cover layer;

reflecting, by the cover layer, a fraction f of ultrasound signals incident thereon (reflected ultrasound signals);

receiving, by the ultrasonic receiver(s), reflected ultrasound signals;

obtaining, by a signal processor, time-of-flight data at least in part from the reflected ultrasound signals; and obtaining, by the signal processor, at least one tactile-related data of the external object from the time-of-flight data;

wherein the time-of-flight data indicate time differences between times of transmission of transmitted ultrasound signals by the ultrasonic transmitter(s) and times of receipt of reflected ultrasound signals by the ultrasonic receiver(s); and the time differences vary in accordance with the ultrasound propagation distance.

19. The tactile-sensing method of claim 18, wherein the tactile-related data is selected from (1) a material characteristic of the external object and (2) rigidity of the external object.

20. The tactile-sensing method of claim 18, wherein:

configuring an ultrasound time-of-flight sensor module additionally comprises configuring a force-measuring element, the signal processor electronically coupled to the force-measuring element; and the method additionally comprises:

obtaining, by the signal processor, impact data from the force-measuring element resulting from the impact and/or contact.

21. The tactile-sensing method of claim 20, wherein:

the force-measuring element is a piezoelectric force-measuring element; and obtaining, by the signal processor, impact data from the force-measuring element comprises obtaining impact data in accordance with mechanical deformation of the piezoelectric force-measuring element resulting from the impact and/or contact.

22. The tactile-sensing system of claim 21, wherein the force-measuring element is a piezoelectric micromechanical force-measuring element (PMFE).

23. The tactile-sensing method of claim 20, wherein the impact data is selected from: (1) time-varying impact force, (2) timing of impact, (3) magnitude of impact, (4) frequency of impact, and (5) rigidity of the external object.

* * * * *